United States Patent [19]

Grajewski et al.

[11] 4,392,096
[45] Jul. 5, 1983

[54] SECTIONAL X-RAY TABLE HAVING DUAL SERVO DRIVES

[75] Inventors: John P. Grajewski, Palmyra, Wis.; Robert J. Loyzim, Hiwassee, Va.

[73] Assignee: General Electric Company, Schenectady, N.Y.

[21] Appl. No.: 311,687

[22] Filed: Oct. 15, 1981

[51] Int. Cl.³ .............................................. G05B 11/32
[52] U.S. Cl. ..................................... 318/625; 318/51; 378/179
[58] Field of Search ...................... 318/625, 51, 55, 58, 318/61, 72, 91; 378/177, 179, 180, 195, 196, 209

[56] References Cited

U.S. PATENT DOCUMENTS

| | | | |
|---|---|---|---|
| 3,068,357 | 12/1962 | Haupt | 378/179 |
| 4,289,997 | 9/1981 | Jung et al. | 318/51 X |
| 4,334,155 | 6/1982 | Geischen et al. | 378/179 X |
| 4,365,345 | 12/1982 | Craig et al. | 378/196 X |

FOREIGN PATENT DOCUMENTS

2026206 9/1979 United Kingdom ................ 318/625

Primary Examiner—B. Dobeck
Attorney, Agent, or Firm—Wheeler, House, Fuller & Hohenfeldt

[57] ABSTRACT

An X-ray table base, an intermediate support mounted on the base for moving bidirectionally, and a carriage with a patient cradle on it mounted for moving bidirectionally on the support. There are individual servomotors for driving the support and cradle, respectively. Each servomotor drives an analog tachometer. The tachometer signals are compared with ramp signals. When, for example, the intermediate support nears the limit of its forward travel, its servo amplifier receives a decreasing ramp signal and the servo amplifier for the cradle motor receives a concurrent increasing ramp signal such that the support decelerates to zero velocity at a predetermined rate and the cradle accelerates to the previous constant velocity of the support at a rate that results in the cradle moving at a constant rate relative to the base.

7 Claims, 7 Drawing Figures

SECTIONAL X-RAY TABLE HAVING DUAL SERVO DRIVES

BACKGROUND OF THE INVENTION

This invention relates to a dual motor, single axis position and velocity servo system for a patient-supporting table that is used to position a patient in an X-ray beam in computed axial tomography and computed projection radiography apparatus, for example.

As is known, in one type of computed axial tomography apparatus an X-ray source is mounted on a scanner base that is journaled for rotation about a nominally horizontal axis on a tiltable gantry. A multiple cell X-ray detector is mounted on the scanner base on the opposite side of the axis from the X-ray source. The X-ray beam emanating from the source is collimated into a fan-shaped configuration that spreads over the circumferential length of the detector and is thin in the direction to which the rotational axis of the scanner base is perpendicular. The patient who is to be examined is customarily supported on an X-ray transmissive table top or cradle in coincidence with the rotational axis of the scanner. The cradle must be supported from a floor-mounted base in a fashion that allows it to be moved in what is called the axial or longitudinal direction relative to the base so that the X-ray beam may be caused to penetrate successive layers of the body. As is well known, the computed axial tomography process requires orbiting the X-ray source and detector jointly about the patient so that the detector will be able to produce analog signals representative of X-ray beam attenuation by the patient for a multiplicity of X-ray source and detector positions that are attained in a 360° orbit in one direction or the other. As is well known, the signals representative of beam attenuation are variously processed with a computer system that yields digital data representative of the intensity of the picture elements that comprise an image in axial perspective of the body layer that has been scanned. The picture element data is converted to analog video signals and is used to display the image on the display screen of a video monitor.

The gantry allows the scanner to be tilted so that the fan-shaped X-ray beam, instead of being projected perfectly vertically, is projected at an angle relative to the horizontal axis to permit imaging angular rather than vertical body layers. Pre-existing computed axial tomography apparatus typically provided for tilting the plane of the fan-shaped beam through an angular range of about 10° from either side of vertical. Since the gantry is a large upright structure, when tilted through a small angle such as 10°, its bottom swings out toward the base on which the axially movable patient-supporting cradle is mounted but the base can be set far enough away from the gantry to avoid having the latter strike the base. This is so because the X-ray transmissive cradle supported the patient in cantilever fashion from the base. However, in a more advanced computed axial tomography apparatus design, tilting of the gantry about 20° or more from either side of vertical has been provided for. Thus, the base that supports the cradle must be set farther away from the gantry to avoid interference by the base when the gantry is tilted through the larger angular range. Hence, in the new design it became necessary to increase the distance through which the patient is translated axially relative to the base. It would be possible to lengthen the cradle so a major part of the patient could be advanced into the X-ray beam but, since the patient would be supported in cantilever fashion, intolerable deflection of the cradle would result. The alternative that was adopted is to make the patient-supporting table assembly in two sections comprised of an intermediate support or carriage that moves relative to the base and a cradle carriage mounted on the intermediate support for moving axially relative to it. The patient cradle itself is an X-ray transmissive member that extends in cantilever fashion from the cradle carriage.

In connection with the computed projection radiography method, using the apparatus described briefly above, the X-ray source and detector are held in a fixed position rather than being orbited to perform a scan as in the computed axial tomography method. In this method, the patient must be advanced through the fan-shaped X-ray beam at a very constant velocity for undergoing a line-by-line scan with a fan beam that is about 1.5 mm thick, for example. As the patient is being advanced, the X-ray detector cells yield analog signals corresponding to X-ray attenuation at closely successive positions of the patient on a line-by-line basis and the resulting attenuation data is stored until the length of the body which is of interest has been scanned. A computer then uses the attenuation data to produce digital data representative of the intensities of the picture elements for all scan lines and these signals are used to drive a video monitor which displays a visual image corresponding to the projected X-ray image. In effect, the computed projection radiography method yields a visual X-ray image that is comparable to the image obtained with ordinary radiographic film but with greather contrast than is obtainable with film because the dynamic range of the X-ray detector is usually greater than that of film.

When a sectionalized patient table comprised of an intermediate support and a cradle functioning in what may be called telescopic fashion is used, the support and cradle must be moved in sequence to move the patient toward or away from the X-ray beam. The preferred thing to do is drive the intermediate support and cradle with individual motors. However, this creates the problem of having one motor come to a stop and having the other motor take over without any change in the translational velocity of the patient. A velocity change would result in an X-ray image that has severe artifacts. The invention described herein solves the problem without degradation of position or velocity accuracy and without the need to use more than one decoder.

SUMMARY OF THE INVENTION

The sectionalized patient support uses a floor-mounted base. An intermediate support or carriage is mounted on the base for being translated axially by means of a servomotor. The X-ray transmissive cradle assembly is mounted on the intermediate support for being translated relative to the latter under the influence of another servo motor drive system. Hereafter, for the sake of brevity, the assembly of the cradle carriage and the X-ray transmissive cradle mounted to it will simply be called a cradle. Initially, both the intermediate support and cradle are retracted away from the gantry to make it convenient for getting the patient on the support and ready for an X-ray examination. When a computed projection radiography scan is to be made, for example, the intermediate support or carriage is driven longitudinally first to begin advancing the patient forward toward or into the fan-shaped X-ray beam. The cradle at first just rides along with the intermediate support. The intermediate support can, of course, be made in a very rugged fashion of X-ray impermeable metal which can support a heavy load in cantilever fashion without significant deflection. When the intermediate support is advanced to a predetermined position under the influence of its servo motor it decelerates to a stop and a cradle drive servo motor accelerates inversely to the deceleration and becomes effective to continue advancing the patient on the cradle which is now moving relative to the intermediate support. During computed projection radiography, the overall velocity of the patient must remain constant even through the intermediate support and cradle are driven with individual motors and are moved in sequence. The invention provides a control system for maintaining patient velocity constant. In other words, the invention provides for making the transition of the intermediate support and cradle movements without allowing any change in the overall velocity at which the patient is selectively translated.

How the general objects of the invention mentioned above and other more specific objects are achieved will appear in the detailed description of a preferred embodiment of the invention which will now be set forth in reference to the drawings.

DESCRIPTION OF A PREFERRED EMBODIMENT

Figure 1:
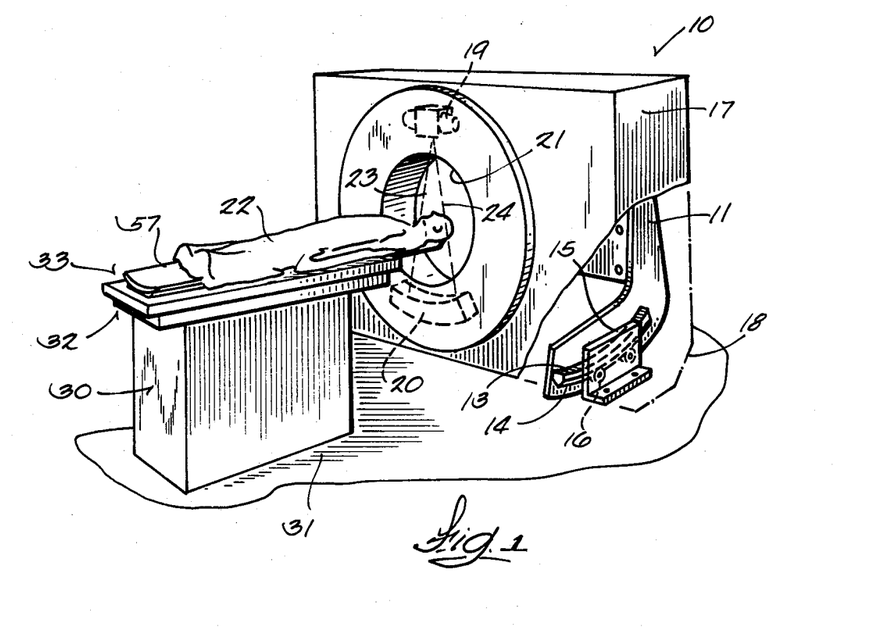
FIG. 1 is a prespective view of a typical computed axial tomography and computed projection radiography scanner together with the new X-ray table assembly with which the scanner cooperates.

Referring to FIG. 1, a typical combination computed axial tomography and computed projection radiography apparatus is designated generally by the numeral 10. The apparatus comprises a gantry including a pair of upright rocker members, one of which, 11, is visible but it should be understood that there is another one laterally spaced from it. A plate 12 spans laterally between upright member 11 and its counterpart. There are rocker members such as the one marked 13 fastened to the upright members. The bottom edge 14 of rocker 13, for example, is V-shaped. A pair of stands, one of which, 15 is shown are fastened to the floor 31. A pair of rollers such as the one marked 16, having V-shaped peripheries are journaled for rotation on stand 15. The V-shaped lower edges of the rocker members 13 rest in V-shaped rollers 16 such that the upright member can be rocked. The drive system for tilting the upright rockers is not shown. By way of example, upright member 11 may be rocked 20° or more in either direction from vertical in the illustrated design.

A housing 17 is effectively supported from the upright members 11 so the housing tilts with them. The lower corners or edges of the housing such as the one marked 18 are slanted so the housing will not strike the floor when it is tilted. Essential components of the apparatus are an X-ray source 19 and a multicell X-ray detector 20. The source and detector are mounted on a scanner base, not visible, which is journaled for rotation on plate 12 so that the X-ray source and detector can orbit jointly about the horizontal axis when a computed axial tomography scan is being performed. The apparatus has a circular opening 21 that is centered on said horizontal axis 15 to provide a passageway for advancing and retracting a patient 22 relative to a fan-shaped X-ray beam whose boundaries are marked 23 and 24. This beam is collimated so it is typically about 1.5 mm thick in the axial or longitudinal direction.

When performing computed axial tomography, the patient is advanced longitudinally in steps so that successive transverse layers of the body may be scanned by joint orbiting of X-ray source 19 and detector 20 while attenuation data is obtained from the detector for permitting reconstruction of an X-ray image of a vertical section of the body. To image body sections at an angle, the gantry is tilted from vertical on rockers 13. When the apparatus is used for performing computed projection radiography where the X-ray source 19 and detector 20 are locked against rotation, the patient must be advanced at a very constant speed through the X-ray beam since the cells in the X-ray detector that provide the attenuation data must be read out at constant time intervals. Thus, the computer, not shown, can relate the body position to the attenuation data and produce an image on television screen, not shown, representative of a projection of the body that is essentially a shadowgraph.

The components of the X-ray table assembly are identified generally in FIG. 1 and are represented schematically. The assembly comprises a base 30 that is mounted on the floor 31. A first carriage or intermediate support 32 is mounted to base 30 in a fashion that permits it to be moved longitudinally, that is, parallel to the axis of rotation of the scanner. A patient cradle 33, made mostly of X-ray transmissive material, is mounted on intermediate support 32 for moving longitudinally in opposite directions relative to the intermediate support. The cradle and intermediate support are driven longitudinally in that order to advance the patient 22 in the forward direction or to the right as viewed in FIG. 1. They are driven in the opposite order to move the patient rearwardly, that is, to the left as viewed in FIG. 1.

Figure 2:
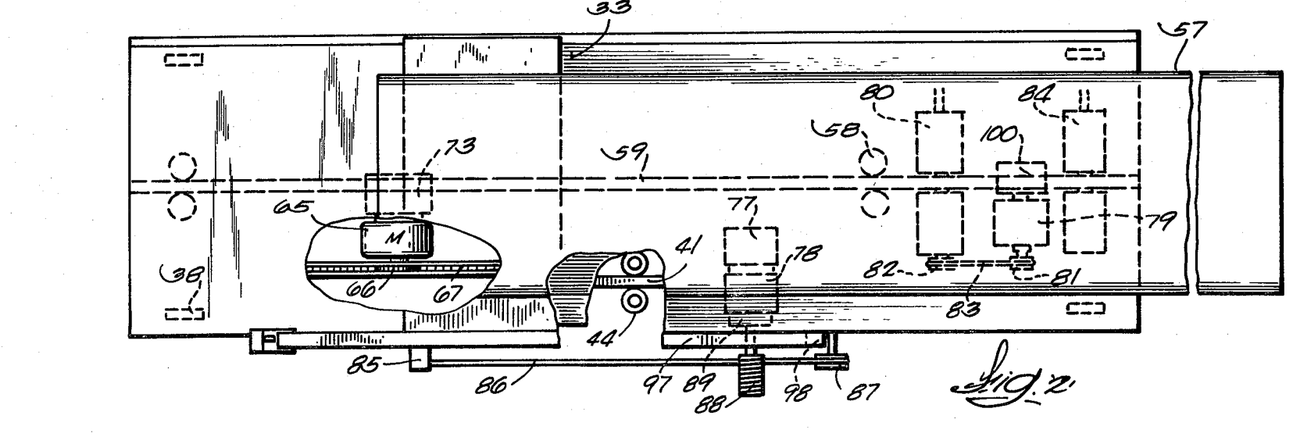
FIG. 2 is a plan view of the patient supporting X-ray table assembly with parts broken away.
Figure 3:
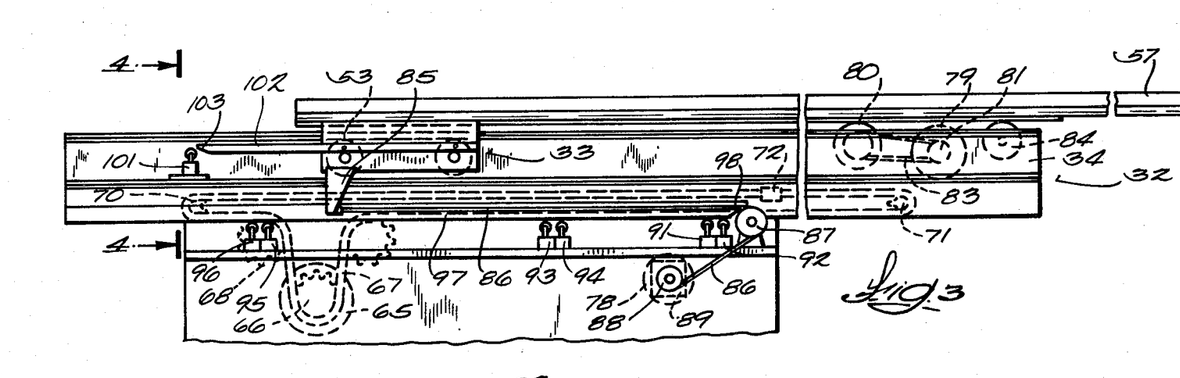
FIG. 3 is a side elevation of the table assembly shown in FIG. 2 wherein the supporting base is partially shown.
Figure 4:
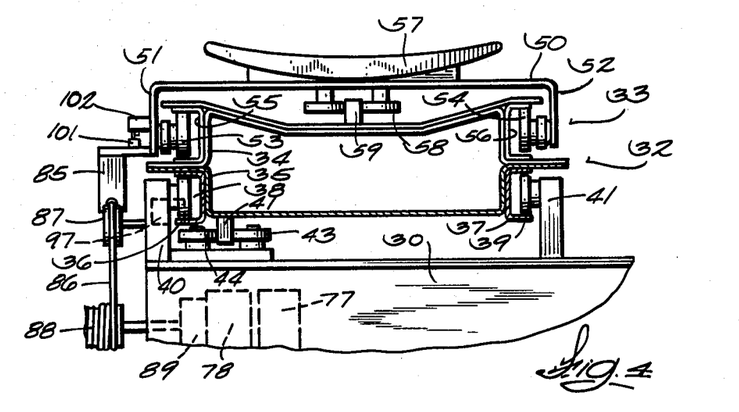
FIG. 4 is a vertical section through the table taken on a line corresponding with 4—4 in FIG. 3.

A more detailed description of the mechanical features of the patient supporting table assembly will now be undertaken in reference to FIGS. 2, 3 and 4. In FIG. 3, one may see that the intermediate support 32 is comprised of two elongated frame members 34 and 35. These frame members are joined with each other and are adapted to translate jointly relative to floor-mounted base 30 under the influence of a servo motor which will be identified and discussed later. Referring to FIG. 4, one may see that there are a pair of channels 36 and 37 fastened to the sides of the intermediate support 32. These channels serve as tracks. The channels run on a plurality of rollers such as those marked 38 and 39 which are journaled for rotation on columns such as those marked 40 and 41. The columns are mounted to the top of stationary floor-mounted base 30. Thus, it will be evident that the intermediate support 32 can translate relative to base 30 on sets of rollers 38 and 39 toward and away from the viewer when looking at FIG. 4 and in the left and right directions when the viewer is looking at FIG. 3. It should be noted that there is a longitudinally extending guide bar 41 fastened to the bottom of frame member 35 of intermediate support 32. Bar 41 has a length substantially coextensive with the length of intermediate support 32. Bar 41 is captured between pairs of rollers such as those marked 43 and 44. The rollers are mounted to the top of base 30 for rotation about vertical axes such that the rollers will cooperate with the bar 41 to prevent lateral shifting of the intermediate support 32.

Referring further to FIG. 4, one may see how the cradle carriage 33 is mounted on intermediate support 32 for independent longitudinal movement relative to the intermediate support. The cradle carriage 33 comprises a channel-like member having a flat top 50 and depending side flanges 51 and 52. A plurality of rollers such as those marked 53 and 54 are mounted for rotation on side flanges 51 and 52. There are a longitudinally extending pair of channels 55 and 56 fastened to intermediate support member 34. It will be evident that the channel member of the cradle assembly can thereby move longitudinally on intermediate support member 32. The curved X-ray transmissive cradle 57 on which the patient is actually supported, is fastened to the top 50 of the cradle carriage. As shown in FIG. 3, metallic cradle carriage 33 is much shorter than the X-ray transmissive cradle 57 so the metallic carriage never gets into the X-ray beam even when the cradle is fully extended relative to the intermediate support. By way of example, cradle 57 is a molded resin product reinforced with graphite fibers to make it strong and yet very X-ray transmissive. Typically, cradle 57 is designed to support a patient in cantilever fashion weighing up to 360 pounds without the cradle deflecting measurably. Deflection would cause the X-ray attenuation data to be inaccurate. Note in FIG. 4 that the cradle carriage 32 is provided with a pair of guide rollers such as the one marked 58. These rollers capture a guide track 59 between them and the track is fastened to the intermediate support 32. Rollers 58 run along the sides of track 59 to guide the cradle carriage 33 in a straight line as it moves relative to intermediate support 32. Means for driving the cradle carriage and intermediate support longitudinally have been omitted from FIG. 4 and will now be discussed in more detail in reference to FIGS. 2 and 3.

In FIGS. 2 and 3, the servo motor for driving the intermediate support 32 in opposite longitudinal directions is marked 65. Motor 65 is mounted to base 30. There is a sprocket 66 fastened to one end of the shaft of servo motor 65. A chain 67 runs on sprocket 66 and over two idler sprockets 68 and 69 that are journaled on base 30. The chain continues in opposite directions from the idler sprockets over another pair of idler sprockets 70 and 71 after which opposite ends of the chain are terminated at a clamp 72 which is fastened to intermediate support 32. It will be evident that reversible servo motor 65 can thereby chain drive intermediate support 32 longitudinally in selected opposite directions. Another end of the shaft of intermediate support drive motor 65 is coupled to a tachometer 73. The tachometer produces an analog voltage whose magnitude is proportional to the rotational speed of servo motor 65 and, hence, to the linear velocity of the intermediate support.

The purpose of the tachometer will be discussed in more detail later.

Figure 5:
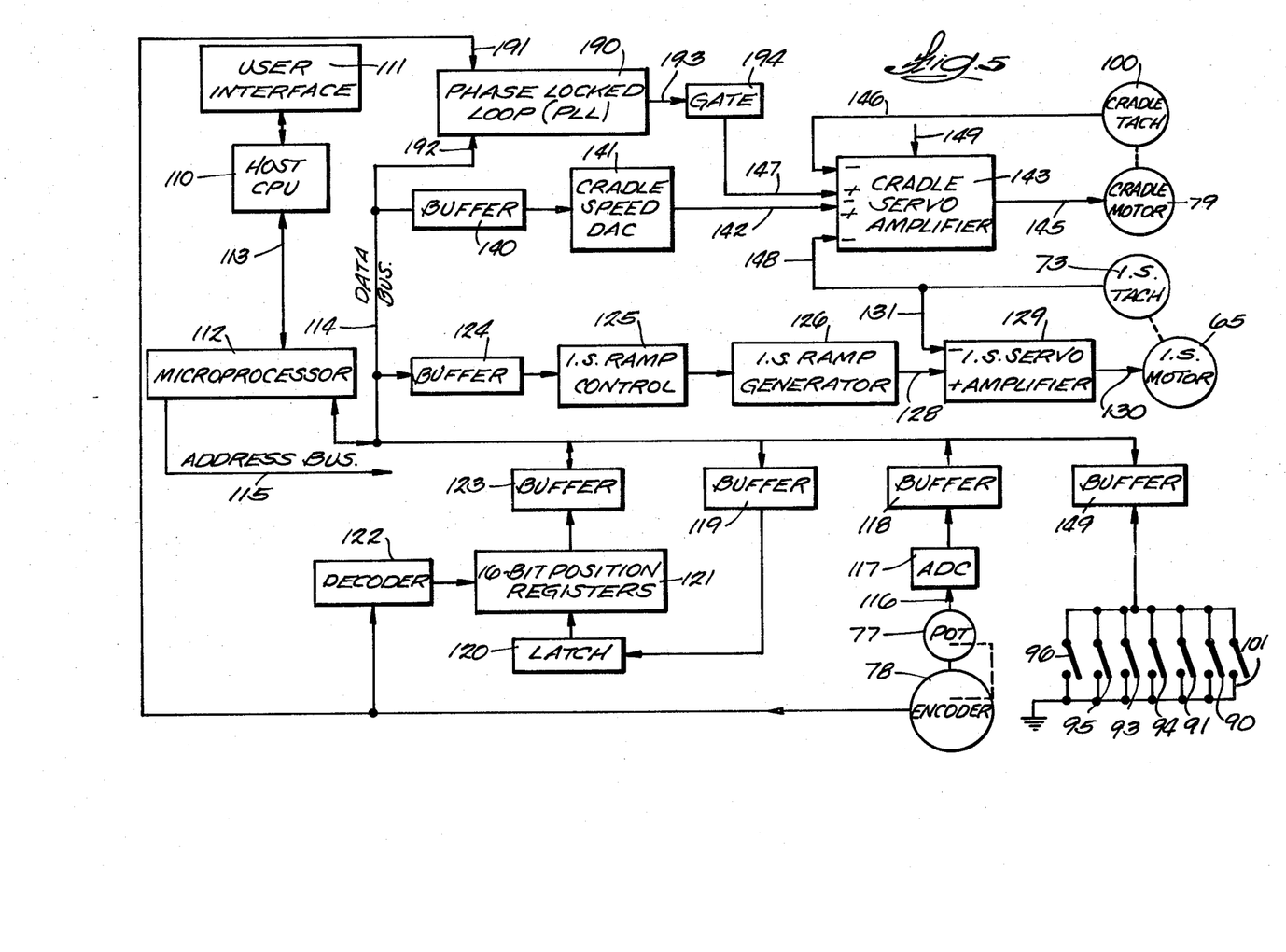
FIG. 5 is a block diagram of the new control system for the extensible intermediate support and cradle components of the X-ray table assembly.

As shown in FIGS. 3 and 5, there is a bracket 85 fastened to cradle carriage 33. The end of a fine cord or cable 86 is fastened to the bracket 85. Cable 86 runs over a grooved idler pulley 87 which is journaled for rotation on base 30. The cable runs from idler pulley 87 to a cable take-up pulley 88 that is on the common shaft of a recoil or take-up spring assembly 89, a pulse encoder 78 and the wiper of a potentiometer 77. When the intermediate support 32 moves to the left relative to the base 30 in FIG. 3, the cable rotates pulley 88 in one direction and winds up the recoil spring in assembly 89. The rotating pulley then drives the potentiometer 77 and encoder 78 in one direction. Then, when intermediate support 32 is driven to the right, the wound up recoil spring unwinds to cause the potentiometer and encoder to rotate in the other direction. As will be explained in more detail later, potentiometer 77 provides an analog voltage corresponding to the longitudinal position of the cradle carriage 33 and its cradle 57 relative to the base 30. Potentiometer 77 is, however, used only for initializing the electronic components of the table assembly drive system as will be discussed in greater detail later. Encoder 78 is of a known type that is adapted to deliver electronic pulses which are counted to permit determining the position of the cradle carriage 33 and, hence, the cradle 57 relative to stationary base 30 as will be discussed in greater detail later. The encoder pulses are coded to provide an indication of the distance that the cradle has travelled longitudinally relative to the fixed base 30. It should be evident that the encoder 78 will be driven at any time the cradle moves, that is, when the cradle moves as a result of the intermediate support 32 on which the cradle is carried being driven and as a result of the cradle being moved along the intermediate support 32. The manner in which the pulses from encoder 78 are used will be discussed later.

The longitudinal drive system for driving the cradle carriage 33 and the patient supporting cradle 57 relative to intermediate support 32 thereon is also shown in FIGS. 2 and 3. The cradle drive system comprises a reversible servomotor 79 which is mounted to intermediate support 32. The axis of the shaft of motor 79 is in parallel with a large friction drive roller 80 which is also journaled for rotation on intermediate support 32 by means which are not shown. Friction drive roller 80 frictionally engages the bottom surface of that part of the cradle 57 which extends away from a cradle carriage 33. Servomotor 79 has a toothed pulley 82 on its shaft. A toothed belt 83 couples pulley 81 in driving relationship with friction roller 80. An idler roller 84, whose journaling means are not shown in detail, provides support under cradle 57 at the outermost point possible on intermediate support 32 to minimize deflection when the cradle 57 is extended in cantilever fashion relative to intermediate support 32 with a patient on the cradle.

Referring further to FIG. 3, there are three pairs of plunger-operated switches, called limit switches, disposed along the path of movement of intermediate support 32. These limit switches are mounted on base 30 and are stationary. The rightmost pair of switches is composed of plunger-operated switches 90 and 91. The switches have rollers on their plungers as shown. Members of another pair of the limit switches are marked 93 and 94. Still another rearmost pair are marked 95 and 96. There is a cam bar 97 fastened to intermediate support 32. The leading end 98 of cam bar 97 is beveled to provide a cam surface for depressing the plungers of the limit switches causing them to switch at appropriate times as the intermediate support 32 translates longitudinally relative to base 30. As will be explained in more detail later, these limit switches are used in the control system for causing the intermediate support to decelerate or accelerate at a rate that is inverse to the rate at which the cradle decelerates or accelerates, respectively, when one or the other of the intermediate support and the cradle is stopping while the other is starting to move such that the patient on the cradle 57 is always moved at a constant velocity toward and away from the X-ray beam path as is required when computed projection radiography is being performed. In FIG. 2, one may see that cradle drive motor 79 drives a tachometer 100 which produces an analog signal proportional in magnitude to the rotational speed of cradle drive servomotor 79. The purpose of tachometer 100 will be discussed in detail shortly hereinafter.

As shown in FIG. 3, another limit switch 101 is mounted to intermediate support 32. This switch is operated by a cam bar 102 that is fastened to cradle carriage 33. The cam bar has a beveled end 103 for camming the roller-plunger of limit switch 101. Limit switch 102 is only improved when the cradle carriage 33 and cradle 57 is being retracted or moved to the left in FIG. 3. The limit switch is actuated when the cradle 33 is within 1 inch of being driven to home position on intermediate support 32. As will be discussed later, limit switch 101 then produces a signal which initiates ramping down or deceleration of the cradle drive and corresponding ramping up or acceleration of intermediate support drive so that the cradle speed remains constant during the transition from driving the cradle to driving the intermediate support.

Before discussing the electronic drive and control system, the general operating mode of the dual-carriage extensible and contractible X-ray assembly will be reviewed. When the patient is to be translated from home position over base 30 forwardly into the X-ray beam as in FIG. 1, the intermediate support 32 undergoes longitudinal driving motion first. The cradle carriage 33 and cradle 57 are just carried with the intermediate support 32 at this time. The intermediate support is accelerated or ramped up to a constant speed during a very short interval. It then travels a predetermined distance to what is called the transition zone and as soon as the intermediate support 32 begins to decelerate the cradle drive motor 80 turns on and causes the carriage 33 and its cradle 67 to accelerate relative to the intermediate support 32 at the same rate that the intermediate support is decelerating relative to the base 30 so that the longitudinal speed of the intermediate support and cradle remains constant relative to the base on which they are supported. The intermediate support drive motor 65 is caused to stop simultaneously with the cradle drive motor 79 reaching its maximum and constant speed. The cradle motor 79 then continues to drive the cradle longitudinally at the same speed at which the intermediate support was formerly being driven. The cradle is then driven to a permissible maximum limit in the longitudinal direction whereupon it is decelerated at a controlled rate and stopped. Thus, the patient is now advanced through the X-ray beam path. The table sections, namely, the intermediate support 32 and cradle 57 are operated in reverse sequence to retract the patient out of the path of the X-ray beam, that is, to move the patient rearwardly or to the left in FIGS. 1-3.

When the patient is to be retracted, the cradle 57 is driven first, back into the intermediate support, and next the intermediate support 32 is driven longitudinally until it reaches its home position which is far to the left of where the intermediate support is presently located in FIG. 3. In the retraction process, the cradle is again driven to a point beginning a transition zone whereupon deceleration of the cradle at a substantially linear rate starats and acceleration of the intermediate support at a corresponding rate starts. However, as in the case of forward motion described in the preceding paragraph, the intermediate support becomes accelerated to its maximum and constant speed at the end of the transition zone so that the patient continues to be moved at a constant speed.

The new dual motor, bidirectional, position and velocity servo assembly will be described in reference to FIG. 5. In this figure, certain electrical components which have been mentioned in connection with describing FIGS. 2 and 3 are represented symbolically and are given the same reference numerals. For instance, encoder 78, potentiometer 77, intermediate support drive motor 65, intermediate support tachometer 73, cradle drive motor 79, and cradle motor tachometer 100, are all represented in FIG. 5. The limit switches are marked 90-96 and 101. For the sake of brevity, hereafter, components associated with the intermediate support drive and control system such as intermediate support motor 65 will be referred to as IS components. For example, intermediate support motor 65 will be called the IS motor.

Refer now to FIG. 5 for discussion of a control system that is applicable to the situation where two support members must be driven in sequence with separate motors where a body on one of the members must not undergo any change in longitudinal velocity even during a transition period wherein one of the members is decelerated to a stop and the other member is accelerated to the velocity of the previously driven member.

In FIG. 5, a host computer is symbolized by the block marked 110 and labelled host CPU. It will be understood that the host CPU is present for performing various functions in connection with the X-ray system as well as being involved in controlling the dual section X-ray table assembly being discussed herein. The user interface is represented by the block marked 111. The user interface will include a keyboard, not shown, by which the use can input instructions that dictate the mode in which the X-ray table assembly is to be operated. For instance, in an actual embodiment of the invention, the user has the option of selecting any one of three longitudinal speeds for the patient cradle and intermediate support combination. Two different cradle travel limits may also be selected. For instance, in one mode, movement of the cradle is limited to 24 inches and in another mode motion is limited to 12 inches of movement in the longitudinal direction.

In FIG. 5, a microprocessor system represented by the block marked 112 provides the intelligence for controlling the cradle and intermediate support servomotors. The data, address and control bus 113 provides for communication between CPU 110 and microprocessor 112. The microprocessor is coupled to a data bus 114 which runs to various electronic components in the control system as is evident from inspection of FIG. 5. Only part of the microprocessor address bus 115 is shown. It will be understood to be coupled to various electronic components in the system that must be addressed.

Assume now that the system is to be powered-up or initialized in preparation for transporting a patient on cradle 57 into and out of the X-ray beam path for making a computed projection radiography scan. The carriage 32 and the patient cradle support or carriage 33 will most likely be in their home position which is farther to the left of the position in which they are shown in FIG. 3. Initial location of the intermediate support and the cradle is immaterial, however, since the system has the intelligence for taking this into consideration. The original location of intermediate support 32 is determined by a corresponding analog signal that is produced by previously mentioned potentiometer 77, hereafter called POT 77. This signal provides a coarse original location reference for the intermediate support. The analog signal from POT 77 is delivered by way of a line 116 to an analog-to-digital converter called ADC 117. This is done on power-up only. Encoder 78 provides position data after power-up. Conversion to a digital position signal is to a 16-bit depth in this embodiment. In response to a proper timing signal from microprocessor 112, the digital position signal is coupled through a buffer 118 to data bus 114 and the microprocessor. Microprocessor 112 then returns the digital position data through a buffer 119 to a latch 120 from which the data is stored in a 16-bit position register 121. Later, when the IS motor 65 begins to drive and the intermediate support 32 begins to move, encoder 78 will be driven to produce a pulse code indicative of the instantaneous or present location of the intermediate support with respect to the original reference obtained with POT 77. The encoded pulse signals are decoded for direction in a decoder 122 and are outputted to the 16-bit position register 121 which would then contain the location of the cradle relative to the base with 16-bit resolution at all times. The signals from the decoder 122 causes the position register 121 data contents to be incremented or decremented depending on which direction the cradle carriage 33 is moving. This position data is coupled to data bus 114 through a buffer 123 so that the position data is continuously available to the microprocessor. When the IS motor 65 is to start, microprocessor 112 brings about production of a ramp signal, that is, an analog signal that varies substantially linearly with time and has a particular slope. The microprocessor determines what the slope should be in response to a command from host CPU 110. As will be evident later, the particular ramp slope elected determines the speed at which the IS motor 65 drives the intermediate support 32 when the support and cradle are to be driven forward together. In the actual apparatus, three different ramps and, hence, three different longitudinal travel speeds for the intermediate support and patient cradle are available.

Assume for the moment that the intermediate support 32 is in its home position and is to be driven forward or to the right where it is shown in FIG. 3. With the support in its starting position cam level 98 would be to the left of leftmost limit switch 96. A command is provided by the host CPU 110 that results in the IS drive motor starting to drive the intermediate support 32. After minor movement of the support, cam bevel 98 actuates limit switch 96. The microprocessor 112 senses operation of limit switch 96, shown in FIG. 5, and produces a logic 1 condition that results in starting generation of the IS ramp signal as indicated by the logic 1 level 133 in the FIG. 6 diagram. As will be evident later, the IS drive motor 65 will then accelerate up to a predetermined constant speed and the intermediate support continues to move. Limit switch 95, adjacent limit switch 96 is employed only when the intermediate support 32 is being retracted back to home position.

Figure 6:
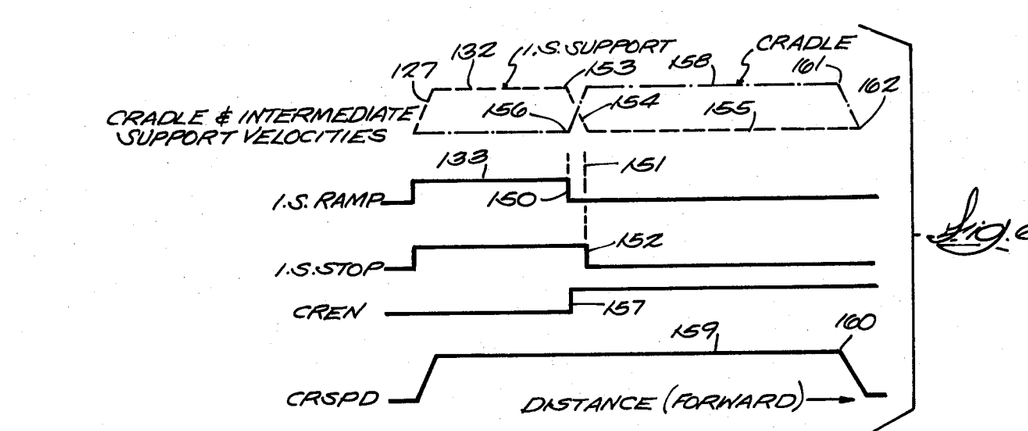
FIGS. 6 and 7 are timing diagrams that are useful for explaining operation of the table drive system.

The command signal for generating the ramp signal that is provided by the microprocessor is fed through a buffer 124 to an IS ramp control symbolized by the block marked 125. The IS ramp control is essentially for triggering and initiating actual production of the IS ramp by IS ramp generator 126. Referring to FIG. 6, the IS ramp is indicated by the dashed line marked 127. Note that the ramp voltage increases with time at this point. The duration of the ramp is indicated by the logic signal 133. The ramp signal from IS ramp generator 126 is output on line 128 to one input of an IS servo motor amplifier represented by the block marked 129. The output of the IS servo motor amplifier provides the power by way of a cable 130 for energizing reversible IS servomotor 65. As soon as the IS ramp analog signal is input to IS servo amplifier 129, IS motor 65 begins to run. At the same time, IS tachometer or IS tach 73 begins to produce an analog signal corresponding to the speed of the IS motor 65. The analog signal from IS tach 73 is fed to another input 131 of IS servo amplifier 129. Since the gain of the servo amplifier 129 is very high, any small difference in input signal is amplified and forces the IS motor 65 to increase its speed. This causes the analog signal from IS tach 73 to increase and it balances the inputs to the servo amplifier 129. Thus, at any time, the sum of the inputs to servo amplifier 129 is essentially zero. Hence, the intermediate support velocity follows the IS ramp generator signal as illustrated by the dashed line 127 in the uppermost diagram in FIG. 6. The constant speed that results is indicated by the dashed line 132 in FIG. 6. The time during which the IS ramp signal is maintained is indicated by the time interval marked 133 in FIG. 6. Since the IS motor 65 is now running at constant speed, the intermediate support 32 is translating longitudinally toward the X-ray beam path at constant speed. This means that the patient is moving at constant speed since the patient is on the cradle 57 and its carriage 33 which is moving with the intermediate support.

Although the IS motor is now driving, the cradle motor 79 is not driving as yet. The manner of making the transition from IS motor drive to cradle drive and for then driving the patient cradle without any change in patient velocity occurring will now be discussed.

Referring to FIG. 5, the microprocessor 112 is programmed to provide another ramp for controlling the cradle speed and drive. This is a digital ramp, however, or a ramp represented by either increasing or decreasing digital values depending on whether the cradle motor is supposed to accelerate or decelerate. The digital ramp for cradle motor activation and speed control, of course, is related to the analog ramp that was provided for the IS motor control since the speeds of the intermediate support and cradle must agree even though they are moved essentially in sequence.

The digital ramp values are sent by microprocessor 112 over data bus 114 to a buffer 140 that outputs to a digital-to-analog converter (DAC) 141 which has the legend "cradle speed DAC". Thus, when the microprocessor determines that the cradle speed ramp should be produced, this ramp will be output on line 142 as a linear analog ramp signal. Until the digital ramp is generated, the cradle motor 79 will be deenergized and the velocity of the cradle relative to the intermediate support will be 0 as indicated by the dash-dot line 144 in FIG. 6. Of course, the cradle on the intermediate support will be moving at the same velocity as the intermediate support. The output of cradle servo amplifier 143 is fed by way of lines 145 to cradle motor 79. Cradle servo amplifier has other inputs besides input 142 from the cradle speed DAC. One input, 146, is from the cradle tachometer 100. Another, 147, is from a phase-locked loop which will be discussed later. Another input 148 is from IS tachometer 73.

The cradle speed ramp is initiated when the microprocessor receives a signal indicating that the intermediate support is near the end of the travel which has been selected for it. This is indicated by the cam surface 98 on cam bar 97 actuating the plunger of limit switch 91. This limit switch 91 and others next to it are shown in FIG. 5 to be coupled through a buffer 149 to the microprocessor data bus 114. The input of an enabling signal to cradle servo amplifier 143 is symbolized by the arrowheaded line marked 149. This enabling signal is provided by the microprocessor and is not absolutely necessary but it guarantees that the cradle motor 79 will not run until the IS motor 65 starts to decelerate at the beginning of the transition period. The cradle enable (CREN) logic signal is indicated by the numeral 157 in FIG. 6.

Assume now that the microprocessor has detected that limit switch 91 has been actuated as a result of the leading tip of the beveled cam surface 98 striking the roller plunger of limit switch 91. This means that the intermediate support 32 is nearly at the end of its selected forward travel limit. Microprocessor 112 responds to operation of limit switch 91 by signaling the IS ramp generator 126 to ramp down as at point 153 in the top line of FIG. 6. The logic level change is at point 151 in FIG. 6. In an actual embodiment, the IS motor is allowed to drive the intermediate support about one more inch after this limit switch 91 is actuated. In FIG. 6, the place where the intermediate support will be stopped is indicated by the dashed line 151 and a line 152 on the IS STOP logic diagram. As stated, when the limit switch 91 is actuated as at point 153 in the velocity diagram of FIG. 6, the IS ramp generator provides a descending ramp voltage that is indicated by the dashed line marked 154 in FIG. 6. The microprocessor 112 responds to operation of limit switch 91 by commanding the IS ramp control 125 to cause the IS ramp generator 126 to produce the ramp down signal. When this happens, the speed of IS motor 65, driving the intermediate support, declines at a uniform rate and finally reaches 0 as indicated by the dashed line 155 in the velocity diagram in FIG. 6. Simultaneously with occurrence of the limit switch 91 being actuated, the cradle servo amplifier 143 is enabled and the cradle speed ramp voltage out of DAC 141 is supplied to the cradle servo amplifier 143 by way of input 142. This starts the servo motor at a point marked 156 in the velocity diagram of FIG. 6 and a corresponding point 157 in the cradle enable (CREN) logic diagram in FIG. 6. The IS tach analog output signal is, as can be seen in FIG. 5, fed to input 148 of the cradle servo amplifier 143. The declining ramp signal from the IS tach is then continuously subtracted from the cradle speed signal 159 in FIG. 6 that is present on line 142 in FIG. 5 which causes the cradle motor 79 to pick up speed at the same rate as the IS motor 65 is losing speed. Note that the sum of the input signals to cradle servo amplifier 143 is always zero. Since the phase-locked signal is zero at this time, the sum of the IS tach signal and the cradle tach signal equals the cradle speed signal from DAC 141 on line 142. At the point 152 in FIG. 6 the IS motor has stopped and the output signal from IS tach 73 is now reduced to 0. The cradle servo amplifier 143 is then controlled exclusively by the cradle speed ramp on its input 142 and cradle motor 79 reaches its maximum constant speed as indicated by the dash-dot line 158 in the cradle velocity diagram of FIG. 6. The intermediate support 32 is now standing still and the cradle 57 is advancing on its carriage 33 at a constant speed forwardly or toward the X-ray beam. The constant total cradle speed is indicated by the line marked 159 in the cradle speed (CRSPD) logic diagram of FIG. 6. The microprocessor has been receiving data indicative of the cradle position relative to the base from the position registers 121 at all times while the cradle is being advanced as a result of the intermediate support being driven and as a result of the cradle being driven along after the intermediate support has stopped. The microprocessor 112 then compares this position data with the maximum position which the cradle is supposed to attain. That is, the microprocessor uses position data to determine when it should start producing a descending ramp to start the short term deceleration of the cradle to a stop. The comparison is made about an inch, for example, before the cradle reaches its limit as determined by the host CPU commands. At this point, indicated by the numeral 160 on the cradle speed diagram in FIG. 6 and by 161 on the cradle velocity diagram, the cradle speed ramp is caused to descend and reach zero as at the point 162 in the velocity diagram of FIG. 6. The cradle and patient are now extended a maximum distance in the forward direction which would have resulted in passing a substantial portion of the patient through the X-ray beam path at constant velocity.

Now that the patient cradle is fully extended, the patient can be retracted to permit making another computed projection radiography line scan in the reverse direction if desired.

Figure 7:
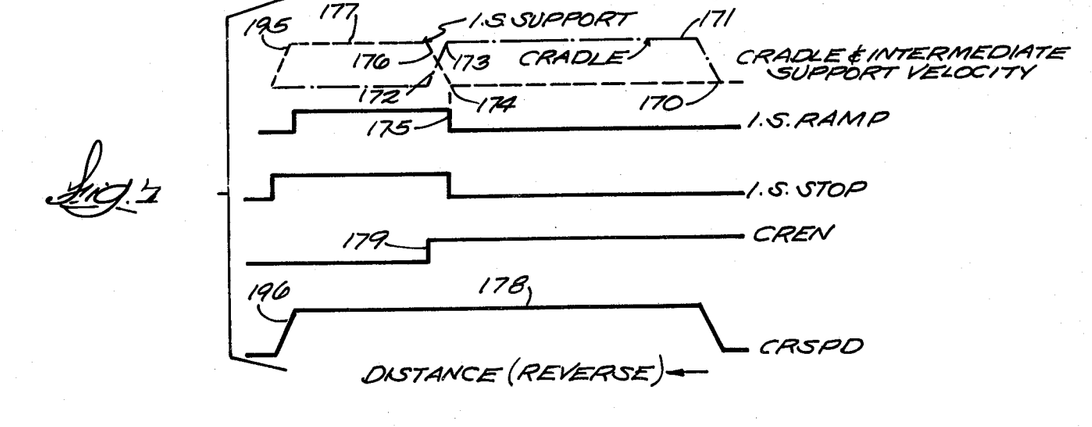

The sequence for retracting the patient rearwardly of away from the X-ray beam path is to move the cradle back into the intermediate support first and then move the intermediate support together with the cradle back to homw position on the X-ray table assembly base 30. The first thing to happen is that the microprocessor receives a command from host CPU software to provide the digital ramp signal to the cradle speed DAC 141 so that the resulting analog ramp signal will be fed by way of input 142 to servo amplifier 143. The point where the servo amplifier is unblocked is marked 170 in FIG. 7 which is now being read from right to left. At point 170 on the cradle velocity curve which is represented by the dash-dot line, the cradle ramp begins to rise and cradle drive motor 79 accelerates at a constant rate. Again, cradle tach 100 produces a corresponding increasingly larger analog signal. This analog signal is continuously subtracted from the cradle speed ramp signal on input 142. Ultimately, the cradle tach signal, when subtracted from the analog ramp signal on input 142 produces a net result of zero and cradle motor 79 runs at a constant speed. Accordingly, the cradle is now being retracted or driven rearwardly at a constant velocity and the cradle motor is running at a constant velocity as indicated by the dash-dot line marked 171 on the cradle velocity curve in FIG. 7. There is another limit switch 101 mounted on intermediate support 32. A cam bar 102 is mounted to cradle carrigge 33. When the retracting cradle carriage 33 is within one inch, for example, of its leftmost limit with respect to intermediate support 32, the beveled end 103 of cam bar 102 operates limit switch 101. The microprocessor detects operation of limit switch 101 and responds by producing logic 1 as at 175 in FIG. 7. This causes the IS ramp generator 126 to generate an acceleration or increasing ramp for the intermediate support drive system. This increasing ramp is subtracted from the cradle speed signal in a fashion previously explained to cause generation of the deceleration ramp for the cradle. Cradle motor 79 then begins to decelerate linearly as indicated by the sloped dash-dot line 172 on the cradle velocity diagram in FIG. 7. At the point 173 where the cradle velocity begins to decline, the intermediate support velocity begins to increase from zero at the point marked 174. Note in FIG. 7 that when the cradle is accelerating up to constant velocity and during the time the cradle is running at constant velocity, the IS ramp is at logic zero which means that the IS motor is not running. Hence, the cradle motor decelerates at the same rate as the IS motor accelerates. Cradle velocity ultimately reaches zero at point 180 on the velocity diagram in FIG. 7 and the IS support velocity reaches a constant value as indicated by the dashed line marked 177 on the velocity diagram. As shown on the cradle speed (CRSPD) diagram in FIG. 7, the cradle, even during the transition period, moves at a constant speed relative to the base 30 of the X-ray table assembly as indicated by the line marked 178 on the cradle speed diagram in FIG. 7. Note that the cradle enable signal designated by the diagram marked CREN that is fed into the cradle servo amplifier as indicated by the numeral 149 in FIG. 5 goes to logic zero at a point marked 179 so that disabling of the cradle drive is guaranteed when the intermediate support reaches constant speed.

Eventually, the intermediate support 32 reaches a pont where the beveled cam surface 98 in FIG. 3 permits actuation of limit switch 95 near the home or fully retracted position of the intermediate support. The microprocessor responds by causing a descending IS ramp signal to be generated and delivered to input 128 of the IS servo amplifier 129. The intermediate support velocity follows this ramp as shown at 195. Since ramp 195 matches ramp cradle speed ramp 196, and the cradle tach input and phase-locked loop signal to the cradle servo amplifier 143 are zero, the sum of all signals at the cradle amplifier are zero.

Limit switches 93 and 94, which were previously mentioned in reference to FIG. 3, serve the same purpose as limit switches 90 and 91 except that switches 93 and 94 are used when it is desired to move the intermediate support a shorter distance before the cradle motor takes effect. In an actual embodiment, limit switches 90 and 91, previously discussed, are used when it is desired to extend the intermediate support 24 inches. Limit switches 93 and 94, on the other hand, are used when it is desired to extend the intermediate support only 12 inches. Host CPU software instructs the microprocessor as to which of the limit switches 90-96, shown diagrammatically to FIG. 6, it should consider as being active.

Yet to be discussed is a phase-locked loop which is present in FIG. 6. The phase-locked loop is used to obtain even greater velocity accuracy than can be obtained with the cradle tach system thus far described. The phase-locked loop is only used during the time that the x-ray source is on while a computed projection radiography scan is being made. Phase-locked loop module is represented collectively by the block marked 190. It has one input 191 from encoder 78. Thus, the PLL receives pulses from the encoder indicative of whether the encoder is counting up or down and it also receives pulses at a rate corresponding to the rate or velocity at which the cradle is moving relative to the X-ray table assembly base. The PLL module has another input 192 from data bus 114. The PLL contains a 1 MHz clock, not shown. It also contains a pair of digital counters, not shown, that are loaded from the data bus with values that can be considered center values. The PLL also contains a comparator, now shown, which compares the encoder 78 pulse rate with the stable crystal clock pulse rate. If there is a difference in the rates, the comparator, not shown, produces signals which either cause the counters to count up or down away from the center value. The output of the counters is fed to a digital-to-analog converter, not shown, but which is in block 190. The ouput of the DAC is zero unless the center value has been counted up or down in which case the analog output of the DAC represents the error value. The error value or signal is fed from output line 193 through a gate 194 to input 147 or the cradle servo amplifier 143. This error signal results in the cradle motor 79 speed being adjusted to a slightly different value than would be the case if the cradle servo amplifier were under the exclusive control of the cradle speed analog signal delivered from cradle speed DAC 141.

It will be evident to those skilled in the art that the control system of FIG. 3 cannot only be used to move the patient through an X-ray beam at constant speed for performing computed projection radiography, but it also can be used for translating the patient to a definite position for making a computed axial tomography scan. It will be evident that what is basically required is that the microprocessor, under control of host CPU software, must provide a cradle speed digital ramp that terminates at a time specified by the microprocessor corresponding with the cradle being in a definite position which is governed by the host computer software when the cradle stops for allowing an orbital scan by the X-ray source and detector. Of course, the IS motor 65 can be controlled in the same fashion in which it was controlled as described heretofore in connection with moving the patient at a constant speed up to a limiting position.

Although an embodiment of the invention has been described in detail, such description is intended to be illustrative rather than limiting, for the invention may be variously embodied and is to be limited only by the claims which follow.

We claim:
1. An X-ray table system comprising:
a base,
an elongated support means mounted to said base for moving longitudinally,
a reversible support means driving motor (support motor) and means for coupling the motor to the support means for moving said support means selectively between a retracted position and an advanced position and back to a retracted position, relative to the base, elongated cradle means mounted to the support means for moving longitudinally relative to said support means, a reversible cradle means driving motor (cradle motor) and means for coupling said motor to the cradle means for moving said cradle means selectively between a retracted position and an advanced position and back to a retracted position relative to said support means, control means for said motors, said control means being operative to activate one of said motors to accelerate up to a constant speed and move the means to which it is coupled to a predetermined position corresponding to the beginning of a transition zone at said constant speed while the other of said motors is inactive, and said control means being operative to decelerate the one motor and accelerate the other motor correspondingly such that at the end of said transition zone said one motor is stopped and said other motor is running at constant speed for moving the means to which it is coupled at constant speed equal to the former speed of the other means.

2. The system set forth in claim 1 wherein said control means for said motors comprise:

digital processor means, and a data bus to which said processor means is coupled, first servo amplifier means (support servo) having a plurality of signal inputs and having power output means coupled to said support motor, second servo amplifier means (cradle servo) having a plurality of signal inputs and having power output means coupled to said cradle motor, first tachometer means (support tach) for producing a signal corresponding to the speed of said support motor and means for coupling said signal to an input of each of said support servo and cradle servo, second tachometer means (cradle tach) for producing a signal corresponding to the speed of the cradle motor and means for coupling said signal to an input of said cradle servo, means for indicating to said processor means when said support is in a plurality of different positions including positions wherein said support is retracted rearwardly relative to said base and wherein said support is advanced forwardly relative to said base to positions on either side of a transition zone, first ramp signal generator means controlled by said processor means in accordance with an indicated position to another input of said support servo a selected one of an increasing or a decreasing ramp signal depending on whether said support motor is to drive said support forward from said retracted position or rearward toward retracted position, said support servo responding to an increasing ramp signal by causing said support motor to accelerate and thereby cause an increasing signal from said support tach until the ramp signal and support tach signals that are input to said support servo balance each other and said support motor is running at and said support is moving forward at a predetermined constant speed, and carrying the cradle means with it, said processor means responding to an indication that said support has reached the beginning of said transition zone by causing said ramp signal generator to start a decreasing ramp signal and said support servo responding by causing said support motor to decelerate and alter the output signal from said support tach correspondingly, second ramp signal generator means controlled by said processor means in accordance with an indicated position to provide to another input of said cradle servo a selected one of an increasing or a decreasing ramp signal representative of the cradle speed, said second ramp signal generator starting to provide an increasing signal to start the cradle motor concurrently with said first ramp generator starting to generate said support motor decelerating signal whereupon said cradle servo has simultaneous inputs of the increasing ramp signal, the increasing cradle tach signal and the decreasing support tach signal, said cradle motor thereby increasing its speed inversely with the decrease in the support tach signal until the support tach signal decreases to zero and the cradle tach signal and the ramp signal to the cradle servo balance and said cradle motor is driving said cradle means at constant speed at the end of the transition zone, and said processor means responding to an indication that said cradle has reached a position near the desired limit of its forward movement by causing a decreasing ramp signal to be provided to an input of said cradle servo to thereby cause said cradle motor to decelerate to a stop.

3. The system as in claim 2 wherein when said cradle is advanced to a forward position and said cradle is to be retracted rearwardly relative to said support and said support is to be retracted rearwardly relative to said base in that order:

said second ramp generator means is controlled by said processor means to provide an increasing ramp signal to an input of said cradle servo to cause said cradle motor to accelerate and to cause an increasing signal from said cradle tach to another input of said cradle servo until the ramp and tach signals balance and the cradle motor is running and the cradle means is moving relative to the support at constant speed, said processor means responding to an indication that the cradle means has reached a position near the end of its travel on said support by causing said second ramp signal generator means to provide a decreasing ramp signal to an input of said cradle servo to thereby decelerate said cradle motor and causing said first ramp generator to provide simultaneously an increasing ramp signal to an input of said support servo to thereby accelerate said support motor inversely to the rate at which said cradle motor is decelerating while the support tach signal is increasing until it balances the ramp signal and said support motor is running at constant speed, said processor means responding to an indication that the support is near the rearward limit of its movement relative to said base by causing said first ramp generator signal means to provide a decreasing ramp signal to said support servo to cause said support motor to decelerate to zero speed.

4. The apparatus defined in any one of claims 2 or 3 including:

an encoder operative to provide pulse signals that are subject to being decoded for providing information about the direction, the position or the rate at which the cradle means is moving relative to said X-ray table base, phase locked loop means operative to compare the encoder pulse rate with a stable clock pulse rate and to produce an error signal representative of any difference between the two pulse rates, means for enabling coupling of said error signal to another of the inputs of said cradle servo concurrently with the cradle tach and ramp signal inputs while said cradle motor is running at constant speed, said cradle servo responding to any error signal by adjusting the speed of the cradle motor by that small amount which results in the cradle motor running at a precisely constant speed.

5. The apparatus defined in claim 4 including:

a potentiometer operatively coupled to said cradle means for producing an analog signal representative of the initial position of the cradle means at the time the system is powered up, an analog-to-digital converter for converting said analog signal to a digital value, said converter being coupled to said data bus, digital register means for storing digital values representative of the position of the cradle means relative to the table base, and means coupling the register means to the data bus to permit the processor means to read cradle position data from the register means, means for transferring the digital data value from said converter to said register when said cradle means is in said initial position, a decoder for decoding the pulse signals from said encoder which signals represent the position and direction of the cradle means when the cradle means is moving with the support and relative to the support, said decoder being operative to increment and decrement to digital value in said register to permit the processor means to determine the exact position of the cradle means when it is moving.

6. An X-ray table system for moving a patient through an X-ray beam path at constant velocity comprising:

a base, an elongated support mounted on the base for moving longitudinally, and an elongated patient cradle means mounted on the support for moving longitudinally relative to the support and to the base, a reversible support drive motor (support motor) and means coupling said motor in driving relation with the support, a first tachometer (support tach) for producing an analog signal representative of the rotational speed of said support drive motor and the velocity of the support, a reversible cradle drive motor (cradle motor) and means coupling said motor in driving relation with said cradle means for said motor to move said cradle means longitudinally relative to the support, a second tachometer (cradle tach) for producing an analog signal representative of the rotational speed of the cradle motor and the velocity of the cradle means relative to the base, servo amplifier means (support servo) for supplying electric power to said support motor, said support servo having a plurality of inputs one of which is an input for the analog signal produced by the support tach, and another input, another servo amplifier means (cradle servo) for supplying electric power to said cradle motor, said cradle servo having a plurality of inputs one of which is an input for the analog signal produced by the support, another for the analog signal produced by the support tach, and other inputs, ramp signal generator means for supplying a selected one of an increasing or decreasing analog ramp signal at predetermined times to said other input of the support servo, a digital-to-analog converter (cradle speed DAC) for supplying an analog signal corresponding to desired cradle speed to one of said other inputs to said cradle servo, a plurality of switches operable, respectively, in response to said cradle means and said support attaining predetermined positions, digital processor means and bus means for communicating digital data and addresses to and from said processor means, a source for supplying a selected one of an increasing or decreasing digital ramp signal, under control of said processor means, to said cradle speed DAC to thereby supply said DAC with a ramp signal having digital accuracy for accurately controlling the speed of said cradle motor, an encoder operated by movement of said cradle for providing pulse signals representative of the direction of movement and position of said cradle means relative to said base, digital position register means for storing digital values corresponding to the position of said cradle means relative to said base and for being read out by said processor means to determine the position of the cradle means, decoder means operative to decode the signals from said encoder and to change the digital position values in said position register means in accordance with movements of the cradle means relative to the base, a potentiometer for providing an analog signal representative of the initial position of said cradle means when said means is not moving, and an analog-to-digital converter for converting said analog signal to a digital value representative of initial cradle position, and means for entering this position data in said register means for being read by said processor means, the operational sequence of said table assembly comprising driving said support first in a forward direction from a retracted positive relative to said base at constant speed to an extended position at the beginning of a transition zone wherein said support motor is decelerated and said cradle motor is accelerated inversely so that the cradle will move forwardly at a constant speed relative to the base even through driving is exchanged between said motors, and for retracting said table assembly the cradle is driven first rearwardly on to the support to the beginning of a transition where cradle motor is decelerated and the support motor is accelerated, said processor responding to one of said switches being operated corresponding to said support being retracted by enabling said ramp generator to generate and supply an increasing analog ramp signal to the input of said support servo to cause said support motor to accelerate and said support tach then supplying an increasing analog signal to the other input of said support servo such that when the input signals balance said support motor will be running at constant speed, said processor means responding to operation of one of the switches at the beginning of said transition zone by enabling said ramp generator to supply a decreasing analog ramp signal to the input of said support servo to decelerate said support motor with a resulting decreasing analog signal from said support tach, said processor means further responding by effecting input of a corresponding digital ramp to said cradle speed DAC for the analog signal therefrom to be supplied to one input of said cradel servo concurrently with the decreasing input signal from the support tach and the increasing signal from the cradle tach such that when said signals balance with the ramp signal said cradle motor drive the cradle means at a constant speed corresponding to the former speed of the support because of the similarity in the slopes of the two ramps, said ramp signal generating sequence being provided oppositely for driving said cradle means rearwardly relative to the support and the support rearwardly relative to the base.

7. The apparatus defined in claim 6 including:

phase-locked loop means having an input for pulses from said encoder, said means being operative to compare the encoder pulse rate with a stable clock pulse rate and to produce an error signal representative of any difference between the two pulse rates, means for enabling coupling of said error signal to another of the inputs of said cradle servo concurrently with the cradle tach and ramp signals while said cradle motor is running at constant speed, said cradle servo responding to any error signal by adjusting the speed of the cradle motor by that small amount which results in the input signals being balanced such that the cradle motor runs at a precisely constant speed.

* * * * *

UNITED STATES PATENT AND TRADEMARK OFFICE
CERTIFICATE OF CORRECTION

PATENT NO. : 4,392,096
DATED : July 5, 1983
INVENTOR(S) : John Grajewski, Robert J. Loyzim & Richard T. Brandt It is certified that error appears in the above—identified patent and that said Letters Patent is hereby corrected as shown below:

Front page, (75) Inventors:, "John P. Grajewski, Palmyra, Wis; Robert J. Loyzim, Hiwassee, Va."
should read
--John P. Grajewski, Palmyra, Wis.; Robert J. Loyzim, Hiwassee, Va.; Richard T. Brandt, New Berlin, Wis.--

Signed and Sealed this

Twenty-second Day of November 1983

[SEAL]

Attest:

GERALD J. MOSSINGHOFF

Attesting Officer  Commissioner of Patents and Trademarks